United States Patent [19]

Forquy

[11] Patent Number: 5,406,000
[45] Date of Patent: Apr. 11, 1995

[54] PROCESS FOR THE PRODUCTION OF 3-AMINOMETHYL-3,5,5-TRIALKYLCY-CLOHEXYLAMINE

[75] Inventor: Christian Forquy, Monein, France

[73] Assignee: Elf/Atochem North America, Inc., Philadelphia, Pa.

[21] Appl. No.: 3,343

[22] Filed: Jan. 12, 1993

[51] Int. Cl.$^6$ .................. C07C 209/26; C07C 209/52
[52] U.S. Cl. ...................... 564/446; 564/448; 564/455
[58] Field of Search .................. 564/446, 448, 455

[56] References Cited

U.S. PATENT DOCUMENTS

| | | | |
|---|---|---|---|
| 3,558,709 | 1/1971 | Höckele | 564/448 |
| 4,772,750 | 9/1988 | Habermann | 564/446 |
| 4,847,291 | 7/1989 | Ingendoh et al. | 514/524 |

FOREIGN PATENT DOCUMENTS

| | | |
|---|---|---|
| 394968 | 10/1990 | European Pat. Off. . |
| 0449089 | 10/1991 | European Pat. Off. . |
| 3011656 | 1/1991 | Germany . |
| 0394967 | 10/1990 | United Kingdom . |

*Primary Examiner*—Peter O'Sullivan
*Assistant Examiner*—Scott C. Rand

[57] ABSTRACT

A method is disclosed for the selective preparation of 3-aminomethyl-3,5,5-trialkylcyclohexylamine by preparing dried 3-cyano-3,5,5-trialkylcyclohexylimine from the reaction of 3-cyano-3,5,5-trialkylcyclohexanone with ammonia in the presence of a drying agent in an amount at least sufficient to retain the water present or generated during the imine-forming reaction, and hydrogenating the dried 3-cyano-3,5,5-trialkylcyclohexylimine in the presence of a cobalt-containing catalyst at elevated temperature and pressure.

11 Claims, No Drawings

PROCESS FOR THE PRODUCTION OF 3-AMINOMETHYL-3,5,5-TRIALKYLCYCLOHEXYLAMINE

BACKGROUND OF THE INVENTION

This invention relates to a process for the manufacture of 3-aminomethyl-3,5,5-trialkylcyclohexylamine. More particularly, it relates to the selective preparation of 3-aminomethyl-3,5,5-trialkylcyclohexylamine by preparing the intermediate, 3-cyano-3,5,5-trialkylcyclohexylimine, in the presence of a drying agent, and hydrogenating the dried imine product to the amine form.

THE PRIOR ART

The 3-aminomethyl-3,5,5-trialkylcyclohexylamines are well-known compounds having utility, e.g., as curing agents for epoxy resins, and as intermediates in the preparation of oil additives, dispersants and the like.

West German patent application 3,011,656 discloses a continuous process for making isophoronediamine (3-aminomethyl -3,5,5-trimethylcyclohexylamine) by reacting 3-cyano-3,5,5-trimethylcyclohexanone with ammonia at a temperature between 40° and 100° C. in the absence of a catalyst to form 3-cyano-3,5,5-trimethylcyclohexylimine and thereafter hydrogenating the imine in the presence of a nickel, cobalt or iron catalyst to form isophoronediamine.

European Patent No. 0,394,967 discloses a two step process wherein 3-cyano-3,5,5-trimethylcyclohexylamine is produced from 3-cyano-3,5,5-trimethylcyclohexanone, as an intermediate, by low temperature catalytic reductive amination, and this intermediate is reduced at higher temperature, or by using a hydrogenation catalyst more reactive toward the nitrile group, to form 3-aminomethyl-3,5,5-trimethylcyclohexylamine.

U.S. Pat. No. 4,429,157, issued Jan. 31, 1984, discloses a process of reacting oxo compounds, such as 3-cyano-3,5,5-trialkycyclohexanone, with ammonia in the presence of an imine-forming catalyst, i.e., an ion-exchanger loaded with ammonia ions or an ammonium salt which is insoluble in the reaction mixture, to form the imine derivative, and reducing the imine to the diamine with ammonia and hydrogen in the presence of a hydrogenation catalyst.

The processes of the first two mentioned prior disclosures provide undesirably high coproduction of the by-product 3-aminomethyl-3,5,5-trimethylcyclohexanol whereas the process of the last mentioned prior disclosure requires high pressure (270-300 bar) as well as an expensive catalyst in the imine-forming stage to obtain high selectivity for the diamine.

SUMMARY OF THE INVENTION

This invention is a process for preparing 3-aminomethyl-3,5,5-trialkylcyclohexylamine in high yields, said process comprising preparing dried 3-cyano-3,5,5-trialkylcyclohexylimine wherein the alkyl radicals are the same or different and have from 1 to 6 carbon atoms, by the process consisting essentially of reacting 3-cyano-3,5,5-trialkyl-cyclohexanone with ammonia in the presence of a drying agent in an amount at least sufficient to retain the water present or generated during the imine-forming reaction, and hydrogenating the dried 3-cyano-3,5,5-trialkylcyclohexylimine in the presence of a cobalt-containing catalyst at elevated temperature and pressure.

DETAILED DESCRIPTION OF THE INVENTION

This invention concerns the high yield preparation of 3-aminomethyl-3,5,5-trialkylcyclohexylamine by reacting ammonia and hydrogen with 3-cyano-3,5,5-trialkylcyclohexanone. The alkyl radical has from 1 to 6 carbon atoms, e.g., methyl, ethyl, propyl, isopropyl, butyl, isobutyl, pentyl, isopentyl, hexyl, isohexyl, and mixtures thereof. Methyl is the preferred alkyl radical based on the greater commercial consumption of the generated product.

The reaction is carried out in a sequential process wherein dried (water-dried) 3-cyano-3,5,5-trialkylcyclohexylimine is first formed by a process consisting essentially of the reaction of 3-cyano-3,5,5-trialkylcyclohexanone with ammonia in the presence of a drying agent. The drying agent has substantially no imine-forming catalytic properties. After forming the imine intermediate, it is hydrogenated in the presence of a classical cobalt-containing catalyst at elevated temperature and pressure.

The drying agents which can be used with this process include, for example, silica gel, alumina, alkaline earth (e.g. calcium, magnesium) oxides, chlorides, bromides, perchlorates and sulfates; zinc chloride or bromide, and the like. Silica gel is preferred as it is more conveniently heat regenerated (at about 160° C.) for reuse. A low-temperature fired alumina can also be advantageously used since it is easily regenerated by heat drying. The drying agent is generally used in large excess in this process since it is readily regenerated and may be repeatedly recycled. In general, the drying agent is used in an amount of from about 5 to greater than 100%, preferably from about 10 to about 50%, based on the weight of the 3-cyano-3,5,5-trialkylcyclohexanone. It can be either fixed in a packed column for use in a continuous reaction system or placed at the bottom of a batch reactor to pick up and separate water evolved during the reaction thereby influencing the reaction equilibrium toward imine formation.

The ratio of the reactants used in the imine-forming process ranges from about one to about 20 moles, preferably from about 2 to about 7 moles, of ammonia for each mole of 3-cyano-3,5,5-trialkylcyclohexanone.

The imine-forming process may be accomplished in a continuous or batch reaction and may or may not incorporate a solvent for one or both of the reactants.

The imine-forming process is advantageously carried out in a mutual organic solvent-for the reactants. The mutual solvent is especially desirable when conducting the reaction in a batch process. Examples of solvents include methanol, isopropanol or any solvent for ammonia and hydrogen, which will not interfere with the reaction. The concentration of the reactants in the solvent is not critical and may range, for example, from about 80 down to about 10 weight percent, preferably from 60 to 20 weight percent, of the total reactants based on the weight of the solution.

The reaction time will range from about 0.1 to about 1 hour, preferably from 0.2 to 0.5 hour depending on the temperature and ammonia pressure. The reaction temperature will range from about $-10°$ to about 50° C., preferably from 0° to 30° C. depending on the ammonia reaction pressure. Generally, the lower the pressure, the lower the temperature required, e.g., a temperature of 0° C. is satisfactory when utilizing an ammonia pressure of 15 psi while a temperature of 30° C. is more satisfactory at 150 psi. The ammonia reaction pressure will generally range between about 10 and 300 psi, preferably between 15 and 150 psi.

Typically, in the imine-forming reaction, ammonia is contacted with the organic solvent solution of dissolved 3-cyano-3,5,5-trialkylcyclohexanone in a pre-reactor containing the drying agent at the selected temperature and pressure. The ammonia is either passed through the reactor, e.g., in a low temperature reaction, or is pressurized in the reactor over a stirred solution of 3-cyano-3,5,5-trialkylcyclohexanone. When the 3-cyano-3,5,5-trialkylcyclohexylimine is formed, the whole solution is usually transferred to the hydrogenation reactor along with the excess ammonia (if any), after separation of the drying agent. If required, the solution can be further dried on a column of drying agent before it is transferred to the hydrogenation reactor.

While the drying agent is the critical supplemental ingredient in the imine-forming reaction and an imine-forming catalyst is not generally used, such catalysts are not detrimental to the reaction and may be employed, if desired.

The hydrogenation step of the sequential process is performed in the presence of a hydrogenation catalyst and pressurized hydrogen. The 3-cyano-3,5,5-trialkylcyclohexylimine and excess ammonia (if present) advantageously remain in solution with the mutual organic solvent during hydrogenation.

The most suitable hydrogenation catalyst is Raney cobalt although any classical cobalt-containing catalyst will function. To improve the activity or the recycling characteristics of the cobalt, the use of nickel-or iron-containing cobalt compositions are preferable as catalysts. In addition, oxides of manganese, titanium, zirconium, chromium, zinc, aluminum and the like can be used as catalyst supports. The catalyst is employed in the hydrogenation step in an amount which generally ranges between about 1 and 25%, preferably 2.5 and 15%, based on the weight of the 3-cyano-3,5,5-trialkylcyclohexylimine intermediate.

The temperature of the hydrogenation is broadly maintained between about 50° to about 140° C., preferably between 60° to 130° C. Hydrogen pressurizes the reaction vessel, in general, within the range of about 150 to about 3000 psi (10.35–207 bars), but preferably, within the range of 300 to 1000 psi (20.7–69 bars). The time allowed for the hydrogenation step is the most important factor for choosing the reaction pressure since the rate of hydrogenation obviously depends on hydrogen pressure. The reaction time generally ranges between about 0.5 and about 8 hours, preferably from 1 to 4 hours in accordance with the amount of pressure used.

The mole ratio of reactants (3-cyano-3,5,5-trialkylcyclohexanone, ammonia and hydrogen, respectively) used in the overall sequential reaction ranges, in general, from 1:1:3 to 1:20:20 but preferably between 1:2:4 to 1:7:10.

The following examples are set forth to demonstrate the invention in one of its embodiments.

EXAMPLE 1

The preparation of 3-aminomethyl-3,5,5-trimethylcyclohexylamine was carried out as follows: 24 g of methanol. and 8.14 g (99.0% area GC) of 3-cyano-3,5,5-trimethylcyclohexanone were put together in a jar having valved tubing connections with a 100 ml. autoclave and a scrubber vessel. The 100 ml autoclave reactor was charged with 2 g of Cobalt-Nickel Raney catalyst (Grace Davison 2700), with the minimum amount of methanol (2 g) required to permit the weighted amount of Cobalt-Nickel Raney catalyst to be poured into the autoclave, and the reactor was sealed. The scrubber was filled with 2.3 g of silica gel (Alpha, large pore, 8–12 mesh, dried at 160° C.). The entire apparatus, i.e. jar, autoclave, scrubber and connection tubing, was purged with inert gas. Then the scrubber and the autoclave were vacuumed sufficiently to assure removal of oxygen from the reactants solution, i.e. 5 inches—vacuum (127 mm. Hg). The methanol mixture from the jar was sucked into the scrubber and 8.7 g $NH_3$ (ammonia) were added (15 psi) by chilling the scrubber at 4° C. over a half an hour period of time, while stirring the solution in the absence of an imine-forming catalyst. The scrubber solution of formed 3-cyano-3,5,5-trimethylcyclohexylimine in methanol was then sucked into the autoclave (the wet silica gel remained in the scrubber). The autoclave was stirred and heated, and 700 psi hydrogen was fed into the autoclave when the temperature reached 60° C. The temperature program set of the autoclave was: 60° C./2h, 80° C./20 mins, 100° C./20 mins, 120° C./10 mins and finally 130° C./1 h and the hydrogen pressure was maintained at 700 psi. The samples were analyzed using a calibrated GC method and the results set forth in the following table.

TABLE

| Sample | Temp. °C. | time hrs. | lights[1] | IPDI[2] | IPAN[3] | IPAA[4] | IPDA[5] |
|---|---|---|---|---|---|---|---|
| 1. | 4 | $t_o$ | — | 96.3 | — | — | — |
| 2. | 120 | 3 | 3.0 | — | 1.1 | 0.8 | 94.8 |
| 3. | | final | 3.1 | — | — | 0.8 | 96.0 |

[1]lights:1,3,3-trimethyl-6-azabicyclo-(3,2,1)-octane (90% of the lights)
[2]IPDI:3-cyano-3,5,5-trimethylcyclohexylimine (cis and trans stereoisomers)
[3]IPAN:3-cyano-3,5,5-trimethylcyclohexylamine (cis and trans stereoisomers)
[4]IPAA:3-aminomethyl-3,5,5-trimethylcyclohexanol (cis and trans stereoisomers)
[5]IPDA:3-aminomethyl-3,5,5-trimethylcyclohexylamine (cis and trans stereoisomers)

EXAMPLE 2 (COMPARATIVE)

Example 1 was repeated in the 100 ml autoclave without the drying step on silica-gel. Thus, 8.0 g of 3-cyano-3,5,5-trimethylcyclohexanone and 24 g of methanol were put together in a scrubber. The 100 ml autoclave was filled with 2 g of Co-Ni Raney catalyst (Grace Davison 2700) with the minimum amount of methanol (2 g) and sealed. The scrubber and the autoclave were vacuumed. Then 8.5 g $NH_3$ were added to the methanol mixture in the scrubber at 4° C. over a half an hour period of time, while stirring the solution. The scrubber solution of 3-cyano-3,5,5-trimethylcyclohexylimine in methanol was sucked into the autoclave which was then stirred and heated, and 700 psi $H_2$ was fed to the autoclave when the temperature reached 60° C. The temperature program set was: 60° C./2h, 80° C./20 mins, 100° C./20 mins, 120° C./10 mins and 130° C./1 h and the hydrogen pressure was regulated at 700 psi. The samples were analyzed with a calibrated GC method. The crude final product contained 90.3% weight 3-aminomethyl-3,5,5-trimethylcyclohexylamine (IPDA), 0.2% weight 3-cyano-3,5,5-trimethylcyclohexylamine (IPAN), 4.0% weight 3-aminomethyl-3,5,5-trimethylcyclohexanol (IPAA) and 5.0% weight 1,3,3-trimethyl-6-azabicyclo-(3,2,1)-octane (lights).

The process of this invention provides novel means for producing 3-aminomethyl-3,5,5-trialkylcyclohexylamine from 3-cyano-3,5,5-trialkylcyclohexanone, ammonia and hydrogen to provide a higher product selectivity and fewer undesirable by-products, particularly 3-aminomethyl-3,5,5-trialkylcyclohexanol, which can be coproduced in a quantity less than 1% by weight of the total crude product. The novel process also lends itself to low pressure hydrogenation apparatus (<700 psi), and requires no catalyst in the imine-forming stage. The process is simplified in its entirety. By drying the imine before it is hydrogenated over a classical cobalt catalyst, the selectivity for 3-aminomethyl-3,5,5-trialkylcyclohexylamine is dramatically improved, and activity is maintained with a classical, inexpensive catalyst at lower hydrogen pressure. Without drying, the imine intermediate, by-product formation is too high with accompanying reduction in product selectivity.

It is claimed:

1. A process for preparing 3-aminomethyl-3,5,5-trialkylcyclohexylamine which process consists essentially of reacting 3-cyano-3,5,5-trialkylcyclohexanone, where the alkyl radicals are the same or different and have from 1 to 6 carbon atoms, with ammonia in the presence of a drying agent in an amount at least sufficient to retain the water present or generated during the reaction, and hydrogenating the dried reaction product in the presence of a cobalt-containing catalyst at elevated temperature and pressure.

2. The process of claim 1 wherein the 3-cyano-3,5,5-trialkylcyclohexanone and ammonia are in solution in a mutual organic solvent during the reaction.

3. The process of claim 2 wherein said mutual organic solvent is methanol.

4. The process of claim 1 wherein the alkyl radicals of the 3-cyano-3,5,5-trialkyl-cyclohexanone are methyl.

5. The process of claim 1 wherein said drying agent is silica gel.

6. The process of claim 2 wherein the reaction of 3-cyano-3,5,5-trialkylcyclohexanone with ammonia is conducted at a temperature of about −10° to about 50° C., a pressure of about 10 to about 300 psi and for a time period ranging between about 0.1 to about 1 hour.

7. The process of claim 6 wherein the alkyl radicals of the 3-cyano-3,5,5-trialkylcyclohexanone are methyl.

8. The process of claim 6 wherein the mutual organic solvent is methanol.

9. The process of claim 6 wherein the drying agent is silica gel.

10. A process for preparing 3-aminomethyl-3,5,5-trimethylcyclohexylamine which process consists essentially of reacting 3-cyano-3,5,5-trimethylcyclohexanone dissolved in methanol with ammonia in the presence of a drying agent comprising silica gel in an amount ranging from about 5 to about 100%, based on the weight of said 3-cyano-3,5,5-trimethylcyclohexanone to form dried 3-cyano-3,5,5-trimethylcyclohexylimine, and hydrogenating said dried imine in the presence of a cobalt-containing catalyst at a temperature of from about 50° to about 140° C. and a hydrogen pressure within the range of about 150 to about 3000 psi for a time period ranging between about 0.5 and about 8 hours.

11. The process of claim 10 wherein the reaction of 3-cyano-3,5,5-trimethylcyclohexanone with ammonia is conducted at a temperature of about −10° to about 50° C., a pressure of about 10 to about 300 psi and for a time period ranging between about 0.1 to about 1 hour.

* * * * *